United States Patent [19]

Fischell et al.

[11] Patent Number: 5,306,259
[45] Date of Patent: Apr. 26, 1994

[54] VASCULAR ACCESS NEEDLE HAVING AN EXTENDED LENGTH BODY

[75] Inventors: Robert E. Fischell, Dayton, Md.; David R. Fischell, Fair Haven, N.J.; Tim A. Fischell, Los Altos, Calif.

[73] Assignee: Cathco, Inc., Dayton, Md.

[21] Appl. No.: 926,271

[22] Filed: Aug. 10, 1992

[51] Int. Cl.$^5$ .............................................. A61M 5/00
[52] U.S. Cl. ..................................... 604/239; 604/164; 604/165
[58] Field of Search ........................ 604/51-53, 604/93, 158-159, 161, 164-166, 239, 240, 272, 280, 900

[56] References Cited

U.S. PATENT DOCUMENTS

| | | |
|---|---|---|
| 1,100,181 | 6/1914 | Hart . |
| 2,578,814 | 12/1951 | Kollsman ............................ 604/125 |
| 2,623,520 | 12/1952 | Bamford, Jr. . |
| 2,658,511 | 11/1953 | Furnell . |
| 2,828,744 | 4/1958 | Hirsch et al. ........................ 604/165 |
| 3,093,134 | 6/1963 | Roehr . |
| 3,454,006 | 7/1969 | Langdon ............................ 604/164 |
| 3,727,613 | 4/1973 | Sorenson et al. . |
| 3,811,441 | 5/1974 | Sarnoff . |
| 3,859,998 | 1/1975 | Thomas et al. . |
| 4,193,399 | 3/1980 | Robinson . |
| 4,274,408 | 6/1981 | Nimrod . |
| 4,468,224 | 8/1984 | Enzmann et al. . |
| 4,534,763 | 8/1985 | Gettig et al. . |
| 4,832,696 | 5/1989 | Luther et al. . |
| 4,850,960 | 7/1989 | Grayzel . |
| 5,045,065 | 9/1991 | Raulerson . |
| 5,137,518 | 8/1992 | Mersch . |
| 5,250,035 | 10/1993 | Smith et al. ........................ 604/164 |

FOREIGN PATENT DOCUMENTS 681640  3/1964  Canada .

Primary Examiner—C. Fred Rosenbaum
Assistant Examiner—Vanitha Alexander
Attorney, Agent, or Firm—Morton J. Rosenberg; David I. Klein

[57] ABSTRACT

This invention is directed to a vascular access needle (20) for insertion of a sharpened end of a needle (28) into the lumen of a blood vessel. The vascular access needle (20) includes both a hollow needle (28) and an elongated cylindrical body (22) having respective central passageway lumen (27) and capillary lumen (26) extending through the entire vascular access needle (20). The elongated cylindrical body includes a planar angled surface (21) which plane is oriented parallel to the plane of the needle distal opening (29), which provides the capability for proper orientation of the needle (28) for insertion into the blood vessel lumen. The elongated cylindrical body (22) further includes a pair of parallel flat surfaces (23) for stabilization and proper orientation of the needle distal opening (29) when inserting into the blood vessel lumen. Further, the elongated cylindrical body (22) is formed of a substantially transparent material composition in order to allow the user to view the displacement of the blood therein subsequent to insertion within the blood vessel lumen.

10 Claims, 2 Drawing Sheets

VASCULAR ACCESS NEEDLE HAVING AN EXTENDED LENGTH BODY

This device is in the field of means and methods for accessing human blood vessels for a multiplicity of purposes including the placement of guide wires, introducer sheaths and catheters.

BACKGROUND OF THE INVENTION

Interventional cardiologists and radiologists currently practice a wide range of procedures that require percutaneous access to the human vascular system. In many of these procedures, percutaneous access occurs at the site of the common femoral artery or vein at the groin for the purpose of passing guide wires and introducer sheaths. Catheters can then be advanced through these sheaths to many places within the human vascular system. One method for performing this procedure utilizes a hollow steel cannula with a separate sharpened stylet needle through its center which is pushed through skin and then completely through the common femoral artery. The stylet is then removed and the steel cannula is pulled back slowly until blood under arterial pressure squirts vigorously in a pulsatile manner out of the cannula's proximal end thus indicating that the cannula's distal end is properly placed within the artery. A guide wire is then placed through the cannula and advanced into the artery, and then the cannula is pulled out. A variety of introducer sheaths and/or catheters can then be advanced over the guide wire and into the arterial system.

Another method for accessing arteries is by means of an introducer needle with a sharpened distal end that does not use a stylet needle. This introducer needle is placed through the skin at the groin and advanced until the opening of its sharpened distal end lies within the arterial lumen. When this occurs, blood squirts forcibly in a pulsatile manner out of the needle's proximal end. The pulsatile blood flow indicates that the introducer needle is properly located in the artery so that a guide wire can be inserted through the introducer needle.

One disadvantage of existing needles is that they have a short, square cross section, optically opaque, plastic handle (or body) which is not comfortable to hold when pushing the needle's sharpened distal end through skin and tissue at the groin. In fact, a typical plastic handle would be approximately 0.8 inches long and would have sharp corners molded into the plastic which are not comfortable to hold while applying considerable squeezing force between the thumb and forefinger while inserting the needle.

Furthermore, because of their short length and opaque body, one cannot see the blood before it squirts out of the needle (when the tip is placed in an artery) until the blood is actually squirting out. The blood squirting out of the cannula at arterial pressure results in a considerable release of blood which can find its way into the eyes, nose, or other mucosal membranes of health care workers in close proximity to the patient. Besides being messy and causing unnecessary blood loss to the patient, the squirted out blood represents a risk to the health care workers who could be exposed to infectious diseases such as HIV carried in the patients blood. Thus minimizing the blood squirting out of the proximal end is highly desirable.

Furthermore, no existing vascular access needles have an indicator as to the angle of the plane of the opening at the needle's distal end.

BRIEF SUMMARY OF THE PRESENT INVENTION

The Ergonomic Vascular Access Needle (EVAN) is designed to overcome the shortcomings of the present vascular access needles. The EVAN has a transparent body with a long central capillary lumen through which blood can be readily observed and through which a guide wire can be inserted after the EVAN needle's distal opening has been placed in the lumen of a blood vessel. Unlike presently used vascular access needles which have a body length of less than 1 inch, the EVAN would typically have a body length which is ideally greater than 2.5 inches. The elongated transparent body makes it possible to see blood about to spurt out from an artery so that the blood flow can be quickly cut off by placing a finger over the EVAN's proximal opening thus reducing blood loss. Furthermore, the EVAN body is contoured to be comfortably held. Still further, the EVAN body has an angled front surface at its distal end that is parallel to the plane of the EVAN needle's distal opening. Furthermore, the EVAN has a thick cylindrical plastic portion of its body that magnifies the image of the blood in the capillary lumen thus making that blood column more visible to the doctor inserting the needle.

Thus, it is an object of this invention to have a vascular access needle with a sufficiently long and contoured body to be comfortably held in the hand while inserting the needle through the skin and into a vascular lumen which greater length also assists in accurately aiming the needle's distal opening into the lumen of a blood vessel.

Another object is to have an angled surface indicator on the device's body which surface is parallel to the plane of the needle's distal opening.

Still another object is to have two parallel flat surfaces within the contoured body which automatically orient the needle's distal opening when the flat surfaces are held between the thumb and forefinger.

Still another object is to have a transparent body with a small diameter central lumen in which the motion of the blood can be readily observed because the body is transparent and also because there is magnification.

Still another object is to be able to quickly cut off blood about to squirt out of the body's long central lumen.

DETAILED DESCRIPTION OF THE DRAWINGS

Figure 1:
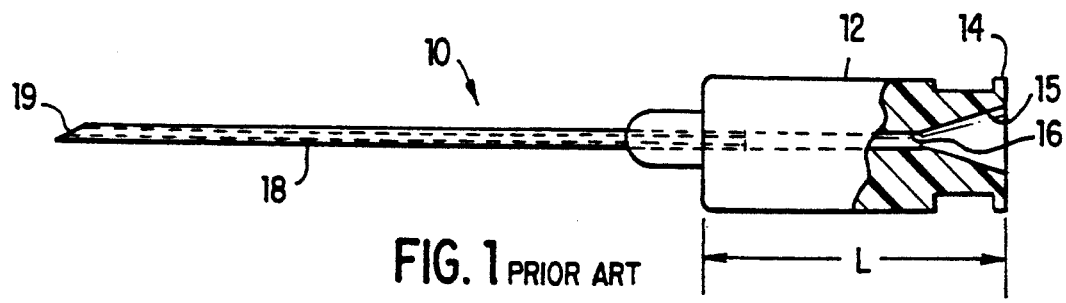
FIG. 1 is a longitudinal, partial cross section of a typical existing vascular access needle.

FIG. 1 illustrates a typical existing vascular access needle 10 having a short opaque, square cross section body 12 with a proximal Luer lock fitting 14 and having a tapered entry hole 15 which leads into the central lumen 16 which extends through the hollow needle 18. The hollow needle 18 is molded into the body 12 and has a sharpened chisel tip which has an opening 19. On the needle body 12 there is typically an indicator as to which end of the needle opening is up but no indication of the plane of the opening at the needle's tip. The body length L is typically less than 1 inch.

Figure 2:
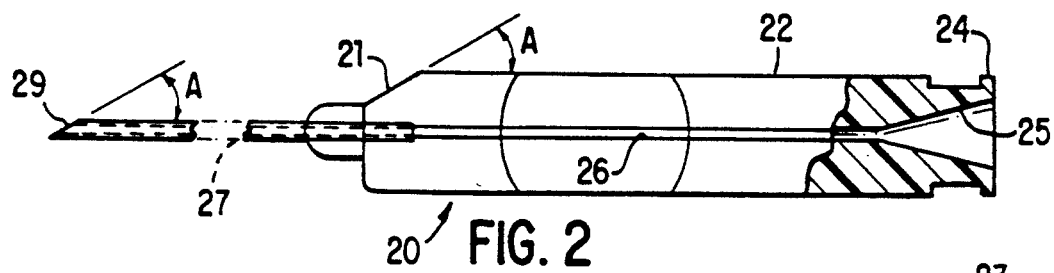
FIG. 2 is a longitudinal, side view, partial cross section of one embodiment of the EVAN.
Figure 4:
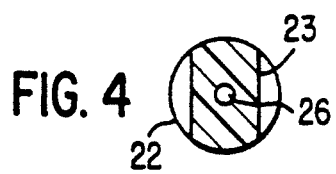
FIG. 4 is the cross section of the EVAN at section 4—4 of FIG. 3.
Figure 3:
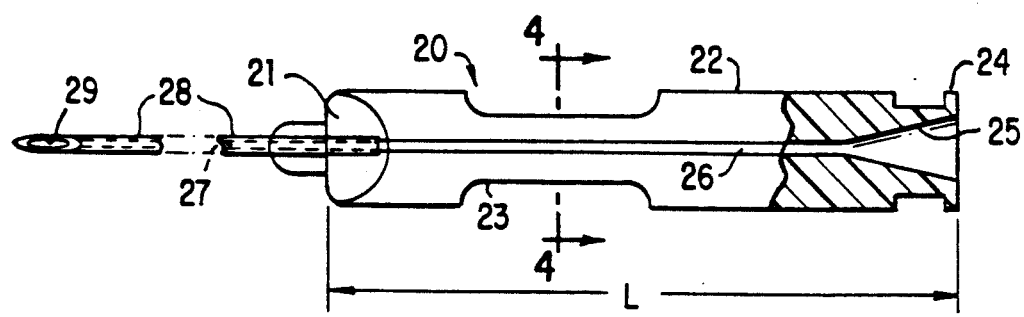
FIG. 3 is a longitudinal, top view, partial cross section of the FIG. 2 embodiment of the EVAN.
Figure 5:
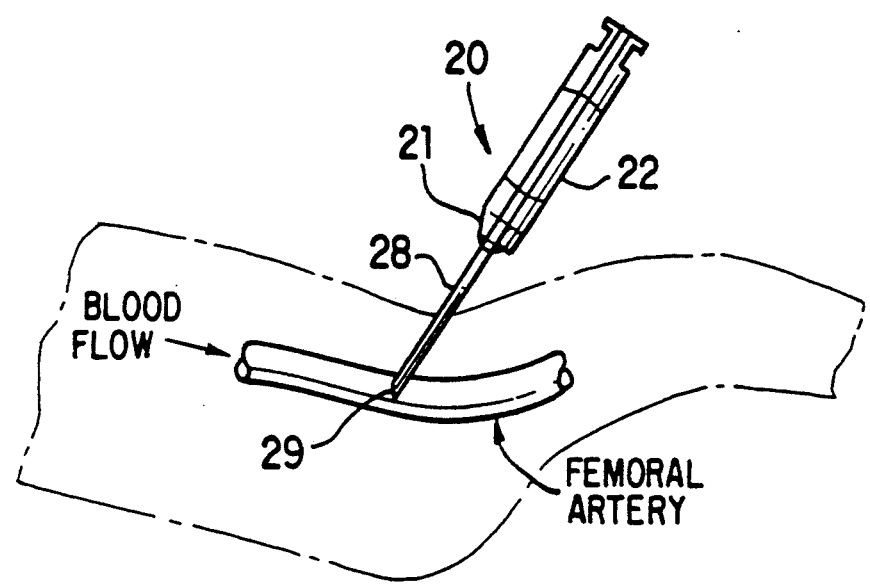
FIG. 5 shows an EVAN percutaneously inserted in the femoral artery at the groin.

FIGS. 2, 3 and 4 illustrate the EVAN 20 having an elongated, generally cylindrical body 22 that typically has a length L that is 2.5 to 3.5 inches but could be as short as 2.0 inches. The body 22 has a proximal Luer lock fitting 24 with a tapered entry hole 25 which leads into the small diameter central capillary lumen 26 which extends into the central passageway lumen 27 of the hollow needle 28 and terminates in the distal opening 29. Although the lumen 26 is shown with a uniform inside diameter, it could be advantageously tapered with a larger diameter at its proximal end. The body 22 has parallel, flat surfaces 23 that can be gripped between the thumb and forefinger so that the surfaces 23 can be vertically placed. This would automatically align the opening 29 either up or down, but certainly not sideways. The angled surface 21 is inclined to the EVAN's longitudinal axis at an angle "A" which is the same angle that the opening 29 is inclined to EVAN's longitudinal axis. If we then look at FIG. 5, we see that when the surface 21 faces toward the patient's head, then the opening 29 is properly oriented relative to arterial blood flow.

Figure 6:
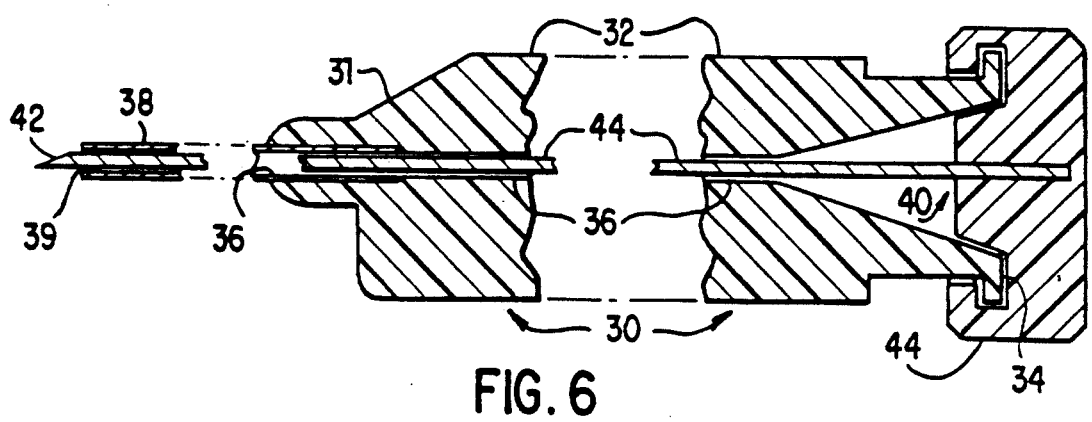
FIG. 6 is a longitudinal, partial cross section of a central stylet embodiment of the EVAN.

FIG. 6 shows an alternative embodiment 30 of the EVAN which differs from the EVAN illustrated in FIGS. 2 and 3 by having a hollow needle 38 which is cut off square at its distal end 39 and is not sharpened; also, there is a stylet 40 having a sharpened distal end 42 whose plane is parallel to the angled plane 31 at the proximal end of the body 32. The stylet body 44 can slide within the lumen 36 and it would be joined to the female Luer lock fitting 34 of the body 32 by a male Luer lock fitting 44 into which the proximal end of the stylet body 42 is molded or adhesively joined. Unlike the EVAN design of FIGS. 2 and 3 which is used to penetrate only the front wall of the blood vessel, in the FIG. 6 embodiment, the needle's distal end 39, including the sharpened stylet end 42, penetrate both walls of the blood vessel. The stylet is then pulled out and then the device is pulled back until needle's distal end 39 is in the vascular lumen. A guide wire is then inserted through the EVAN's central lumen into the vascular lumen and the EVAN is pulled over and off the guide wire's proximal end. A hollow stylet having its own extremely small diameter central lumen is also envisioned.

For all EVAN embodiments, proper placement of the needle's distal tip in the lumen of a vein is determined by attaching a syringe to the Luer lock fitting 24 or 34, exerting a suction and observing the blood pulled into the small diameter capillary lumen. Proper placement of the EVAN's distal opening 29 or 39 in an arterial lumen is determined by noting rapid motion of the blood column through the lumen 26 possibly followed by pulsatile blood squirting out of the EVAN's proximal end. Because the body 22 would typically be fabricated from a transparent plastic such as polymethyl methacrylate (typically known as acrylic, Lucite, or Plexiglass) it is easy to see the blood within the body's central lumen. Visibility is further enhanced because the curved, cylindrical surface of the bodies 22 and 32 and the thickness of the clear plastic cause a magnification of the diameter of the central lumens 26 or 36. A thickness of the plastic wall of at least 0.080 which would provide the desired magnification. This design reduces blood loss when accessing veins and also facilitates knowledge of when the blood is about to squirt out when accessing arteries so that the flow can be cut off somewhat more quickly.

Various other modifications, adaptations, and alternative designs are, of course possible in light of the above teachings. Therefore, it should be understood at this time that within the scope of the appended claims, the invention may be practiced otherwise than as specifically described herein.

What is claimed is:

1. A device for accessing a vascular lumen comprising:

a hollow needle having a distal end, a central passageway, and a proximal end and having a distal opening whose plane lies perpendicular to the needle's longitudinal axis, the opening being joined to the needle's central passageway which said central passageway has distal and proximal ends;

an elongated plastic body having distal and proximal ends and having a central lumen extending therebetween, the central lumen having distal and proximal ends and being joined at its distal end to the proximal end of the needle's central passageway thus forming an unobstructed passageway through the device, the elongated body having a length of at least 2.0 inches and being contoured so that the elongated plastic body can be comfortably held between a thumb and a forefinger of one hand with these fingers pushing against only smooth surfaces of the body, the body further having a Luer fitting at its proximal end; and, a stylet having a body with a sharpened distal end and a Luer fitting at its proximal end, the stylet's body being adapted to move slideably through the central lumen of the plastic body, the stylet further being adapted to have its proximal Luer fitting mate with the Luer fitting at the plastic body's proximal end.

2. The device of claim 1 having a body length of at least 2.5 inches.

3. The device of claim 1 further comprising a plastic body which is optically transparent.

4. The device of claim 3 wherein the optically transparent plastic is polymethyl methacrylate.

5. The device of claim 1 further comprising an angled surface at the body's distal end whose plane is parallel to the plane of the stylet's distal end.

6. The device of claim 1 further comprising a generally cylindrical body which has 2 flat, parallel surfaces formed near the center of the length of the body, said flat parallel surfaces being oriented so that a line normal to the plane of the opening at the needle's distal end is oriented parallel to the plane of said flat parallel surfaces.

7. The device of claim 1 wherein the central lumen of the device is tapered to a larger diameter at the lumen's proximal end.

8. A device for accessing a vascular lumen comprising:
   (a) a hollow longitudinally extending needle having a longitudinal axis defining a needle distal end and a needle proximal end and a longitudinally directed central passageway extending therethrough, said needle distal end forming a substantially planar needle distal end surface being inclined with respect to said longitudinal axis; and,
   (b) an elongated rigid substantially transparent body defining a body distal end and a body proximal end and a longitudinally directed central lumen extending therethrough, said transparent body distal end being coupled to said needle proximal end, said body central lumen and said needle central passageway being aligned in fluid communication with each other for providing a longitudinally directed through passageway, said distal end of said transparent body forming a planar surface substantially parallel to a plane of said needle distal end surface.

9. The device as recited in claim 8 where said elongated rigid substantially transparent body includes:
   (a) at least a first longitudinally extending section being arcuately contoured in cross-section; and,
   (b) a second longitudinally extending section formed in one piece with said first section, said second section having a pair of longitudinally directed planar sidewall surfaces adapted to be grasped between a thumb and forefinger of a hand of a user, said planar sidewall surfaces defining a pair of sidewall surface planes extending parallel to a line directed normal to a plane of said inclined needle distal end surface.

10. The device as recited in claim 8 where said transparent body has a longitudinal length of at least 2.0 inches.

* * * * *